(12) United States Patent
Chen

(10) Patent No.: US 11,044,912 B2
(45) Date of Patent: *Jun. 29, 2021

(54) BRANCHED POLYMERIC BIGUANIDE COMPOUNDS AND THEIR USES

(71) Applicant: Hwang-Hsing Chen, Allen, TX (US)

(72) Inventor: Hwang-Hsing Chen, Allen, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 16/476,025

(22) PCT Filed: Dec. 20, 2017

(86) PCT No.: PCT/US2017/067678
§ 371 (c)(1),
(2) Date: Jul. 3, 2019

(87) PCT Pub. No.: WO2018/128823
PCT Pub. Date: Jul. 12, 2018

(65) Prior Publication Data
US 2019/0373895 A1    Dec. 12, 2019

Related U.S. Application Data

(60) Provisional application No. 62/498,580, filed on Jan. 3, 2017.

(51) Int. Cl.
*A01N 47/44* (2006.01)
*A61K 8/84* (2006.01)
*A61K 9/00* (2006.01)
*A61K 47/34* (2017.01)
*C08G 73/06* (2006.01)

(52) U.S. Cl.
CPC .............. *A01N 47/44* (2013.01); *A61K 8/84* (2013.01); *A61K 9/0048* (2013.01); *A61K 47/34* (2013.01); *C08G 73/065* (2013.01); *A61K 2800/524* (2013.01)

(58) Field of Classification Search
CPC .......... A01N 47/44; A61K 8/84; A61K 9/004; A61K 47/34; A61K 2800/524; C08G 73/065
See application file for complete search history.

(56) References Cited

U.S. PATENT DOCUMENTS

| 6,309,596 B1 | 10/2001 | Xia et al. |
| 6,369,112 B1 | 4/2002 | Xia |
| 8,642,771 B2 | 2/2014 | Gridnev |
| 9,328,200 B2 * | 5/2016 | Chen ............... C08G 73/02 |
| 2008/0311070 A1 | 12/2008 | Burke et al. |
| 2011/0124772 A1 | 5/2011 | Wang |
| 2011/0263717 A1 | 10/2011 | Fridman |

FOREIGN PATENT DOCUMENTS

| CN | 103843808 A | | 6/2014 |
| WO | 9820738 A2 | | 5/1998 |
| WO | 9924542 A1 | | 5/1998 |
| WO | WO 98/20738 | * | 5/1998 |
| WO | 2012047630 A2 | | 5/1999 |
| WO | 9820738 A1 | | 4/2004 |
| WO | 2012047630 | * | 4/2012 |
| WO | 2012047630 A2 | | 4/2012 |
| WO | WO 2013/054123 | * | 4/2013 |

OTHER PUBLICATIONS

International Search Report and Written Opinion in Related International Application No. PCT/US17/67678, dated Apr. 18, 2018, 15 Pages.

First office action in related Chinese patent application No. 201780081544.7, dated Sep. 16, 2020, 11 pages.

* cited by examiner

*Primary Examiner* — Shirley V Gembeh

(74) *Attorney, Agent, or Firm* — Law Office of Jeff Williams PLLC; J. Oliver Williams

(57) ABSTRACT

Biocidal branched polymeric biguanide compounds are made by polycondensation of sodium dicyanamide and a Afunctional primary amine and/or a tetrafunctional primary amine and optionally with a difunctional primary amine. The branched polymeric biguanide compounds have 2-dimensional conformation that provides better coverage over the surfaces of microorganisms and enhances efficacy as biocides as compared to most commercially available linear (one-dimensional) polymeric biguanide compounds. The bulkier 2-dimensional conformation of this invention limits the uptake, accumulation and release of these branched polymers to and from contact lenses. Therefore, these branched biguanide polymers can reduce the cytotoxicity, enhance compatibility and suitable for ophthalmic use. The highly branched polymers can be prepared with minimum or no difunctional primary amines. The lightly branched polymers can be prepared with of a minimum ratio of trifunctional plus multifunctional primary amines to difunctional primary amines.

6 Claims, No Drawings

BRANCHED POLYMERIC BIGUANIDE COMPOUNDS AND THEIR USES

CROSS-REFERENCE TO RELATED APPLICATION

Field of Invention

The present invention relates to biocidal branched polymers comprising polymeric biguanide. The branched polymeric biguanide are made by polycondensation of sodium dicyanamide and a trifunctional and/or a tetrafunctional primary amine and optionally with a difunctional primary amine to control the number of branches. The branched polymeric biguanide can also be made by polycondensation of guanidine hydrochloride and a trifunctional and/or a tetrafunctional primary amine and optionally with a difunctional primary amine to control the number of branches. The preferred tetrafunctional primary amines include 3,3',3",3"'-(ethane-1,2-diylbis(azanetriyl))tetrakis(N-(2-aminoethyl) propanamide), N1,N1'-(ethane-1,2-diyl)bis(N1-(3-aminopropyl)propae-1,3-diamine), and N2,N2'-(propane-1,3-diyl) bis(N4,N6-bis(3-aminopropyl)-1,3,5-triazine-2,4,6-triamine). The preferred trifunctional primary amines include propane-1,2,3-triamine, pentane-1,3,5-triamine, $N^1,N^1$-bis(2-aminoethyl)-ethane-1,2-daiamine, $N^2,N^4,N^6$-tris(6-aminohexyl)-1,3,5-triazine-2,4,6-triamine, $N^2,N^4,N^6$-tris(6-aminopropyl)-1,3,5-triazine-2,4,6-triamine, $N^2,N^4,N^6$-tris(6-aminobutyl)-1,3,5-triazine-2,4,6-triamine, $N^2,N^4,N^6$-tris(6-aminoheptyl)-1,3,5-triazine-2,4,6-triamine, $N^2,N^4,N^6$-tris(6-aminopentyl)-1,3,5-triazine-2,4,6-triamine. The preferred difunctional primary amines include hexane-1,6-diamine, pentane-1,5-diamine, butane-1,4-diamine, propane-1,3-diamine, ethane-1,2-diamine, heptane-1,7-diamine.

The branched polymers exhibit higher biocidal efficacy especially against algae and fungi presumably because of the better surface coverage of the microorganisms. The branched polymers exhibit higher molecular weight as compared to non-branched (linear) polymers and have higher biocidal efficacy. The branched polymers have 2-dimensional network and can improve compatibility with sensitive tissues and are highly safe for the eyes and skin, and have a negligible adsorption onto contact lenses and suitable for ophthalmic and cosmetic uses.

BACKGROUND ART

A biocide is a chemical substance, which can deter, render harmless, or exert a controlling effect on any harmful organism. Biocides are commonly used in medicine, agriculture, forestry, and industry.

The development of new and useful biocides requires consideration of many elements such as the following: the type of organism whose control is desired; the manner in which the biocide is to be deployed; the costs of preparing and delivering the biocide; environmental or disposal issues; and so on. Depending on the potential use envisioned, primary considerations are likely to include both its potency against the organisms targeted, as well as its biocompatibility, e.g. lack of toxicity against the humans or animals which may come into contact with it. Biocides may have a broad or narrow spectrum of activity.

Many of the current organic biocides have two functional group components, a hydrophilic/polar part and a hydrophobic/oil part. Broad-spectrum biocides may require higher hydrophobic elements in order to penetrate biological membranes and achieve their full potency. Hydrophobicity in biocides can be achieved through incorporation of long chain hydrocarbons or aryl groups into the structure of the molecule. However, the current organic biocides used in the pharmaceutical field are focused on improving biocompatibility to reduce the toxicity against human tissues. Discovery of biocides with a desired balance between hydrophilicity and hydrophobicity for its field of use is important and highly challenging.

Polyhexamethylene biguanide (PHMB) is one of the most common and potent biocide being used in the ophthalmic solution and cosmetic application. Although higher MW is necessary for higher efficacy, the average polymer length of PHMB is only about 5 (Journal of Applied Bacteriology 1990, 69, p 593-598) or 12 (British Journal of Environmental Sciences Vol. 4, No 1, pp. 49-55, February 2016). The small molecule of PHMB facilitates penetration and accumulation readily into contact lens or skin and causes irritation when worn in the eye or applied on skin.

For their potential in overcoming some of the disadvantage of the smaller organic monomeric biguanide compound described above, polymeric bigunide compounds has been investigated for a number of years.

For example, U.S. Pat. No. 9,492,771 B2 discloses "Polyethtyleneimine and polyalkylene biguanide ligand graft functionalized substrates" are useful in selectively binding and removing biological materials, such as viruses, from biological samples.

WO 99/24542 discloses polyhexamethylene biguanide with alkylamine capping groups at the two ends of the polymer.

WO 2017/163091 A1, WO 2015/044669 A1, WO 2013/054123 A1 disclose a composition for use in the treatment of fungal infection comprising a polymer/nanoparticle with linear or branched backbone that has terminal monoguanide, guanidine and biguanide groups.

WO 2017/141,204 A2 discloses an entry-promoting agent comprises a liner and/or branched dendrimeric polymer with grafted/crosslinked biguanidine moieties.

U.S. Pat. No. 9,278,079 discloses an ocular composition consisting polyhexamethylene biguanide. The composition can be applied to a fabric pad for use as an eyelid cleanser, where the fabric pad is pre-moistened with the composition and packaged for use. The composition may also be used in an eyelid treatment kit for convenient combination treatments to improve overall eyelid hygiene and adjunctive eyelid therapy.

WO 2012/047630 A2 discloses uses of linear or branched polymer with guanide, biguanide or phenylguanide as capping groups for anti-bacterial/HIV infection.

WO 00/35862, WO99/24542, U.S. Pat. Nos. 8,440,212, 7,951,387, 6,503,952, 6,303,557, 6,010,687, 5,922,693, 5,885,562, 5,668,084, 5,529,713, 5,470,875, 5,356,555, and 5,141,803 disclose compositions consisting of polyhexamethylene biguanide for antimicrobial, wound dressing, cleaning and deodorant uses.

U.S. Pat. No. 5,453,435 discloses a preservative system consisting of polyhexamethylene biguanide for use in contact lens solutions.

However, polyhexamethylene biguanide is known to be irritating to ocular tissues. All of the prior art are related to linear polymeric biguande compounds and compositions but none of branched polymeric biguanide compounds are disclosed. There still exists a need for biocides with useful antimicrobial activity; non-irritating; low toxicity; compatibility with the materials and tissue with which they come into contact.

SUMMARY OF THE INVENTION

The present invention is directed to branched polymeric biguanide compounds. In particular, this invention relates to new polymeric biguanide compounds, which contain branched biguanide groups with 2-dimentional networks for the maximal surface coverage of the microorganisms to enhance antimicrobial efficacy and for minimal uptake, accumulation and release of contact lenses to enhance ocular safety. The present invention also relates to the use of these compounds as biocide in the industry, especially in pharmaceutical, cosmetic and lens care products. In particular, the present invention relates to the use of these new compounds as preservatives for ophthalmic, otic, cosmetic or nasal compositions and as disinfectants for contact lens care products.

The compounds of the present invention differ from prior compounds through the introduction of branched biguanide groups. Without wishing to be bound by theory, it is thought that the branched biguanide groups may increase antimicrobial efficacy by maximal surface coverage with the two dimensional conformation and enhance ocular comfort by minimum uptake and release on contact lenses. Other features and advantages of the invention will become apparent from the following detailed description and claims.

DESCRIPTION OF THE INVENTION

The novel biocides of this invention comprise a polymer having at least one of branched biguanide units of the following formula:

wherein Linker3+ represent linkage group with 3, or 4 points of connections for biguanide groups and at least 1% of the Linkers has 3 or 4 connections;

Linker2+ represent independently the same or different linkage groups with 2, 3, or 4 points of connections for biguanide groups;

Linkers represent the sum of Linker3+ and Linker2+;

Linkers represent synthetic/non-natural linkage groups and has a molecular weight of less than 1000;

l, m, n represent integer varying from 1 to 100, preferably from 1 to 20.

The preferred biocides of the present invention comprise a branched biguanide polymer of the following units:

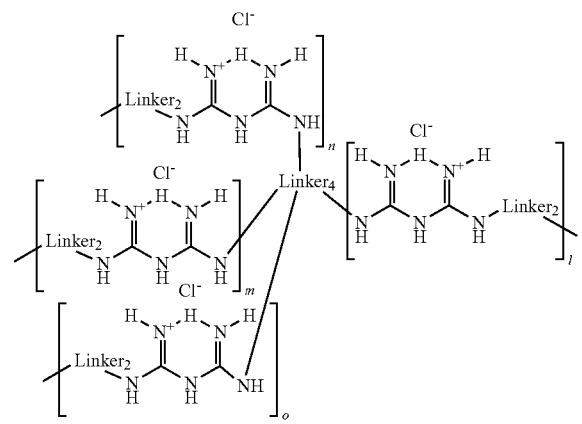

Formular 2

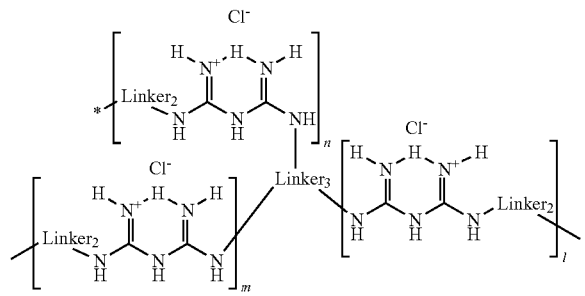

Formular 3

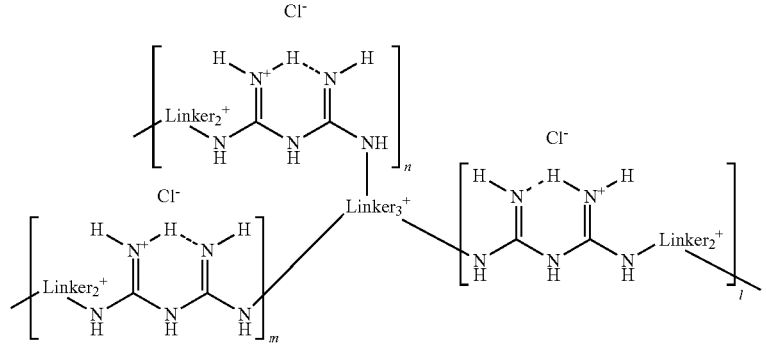

Formula 1

-continued

Formular 4

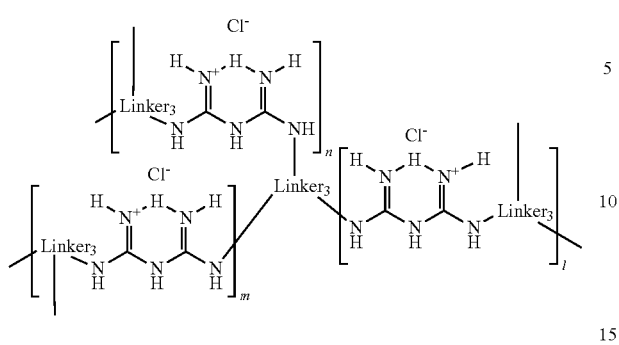

wherein Linker4 represent linkage group with 4 points of connections for biguanide groups and at least 1% of the Linkers has 4 points of connections in Formular 2;
Linker3 represent linkage group with 3 points of connections for biguanide groups and at least 1% of the Linkers has 3 or more connections in Formular 3;
Linker2 represent independently the same or different linkage groups with 2 points of connections for biguanide groups;
Linkers represent the sum of Linker4, Linker3 and Linker2;
Linker4 independently represent
Linker4

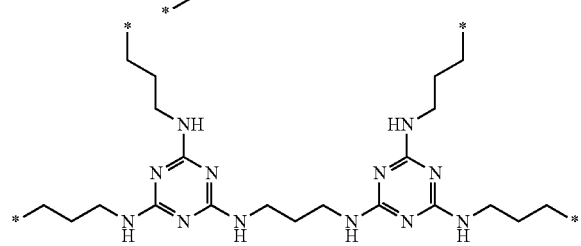

Linker3 independently represent
Linker3

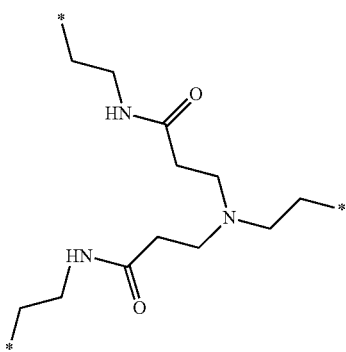

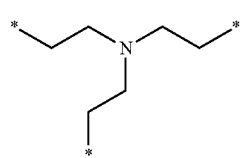

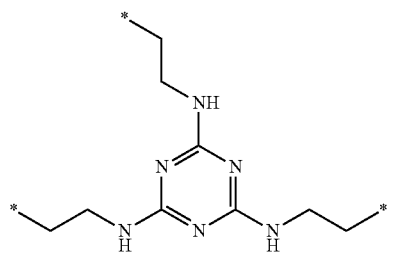

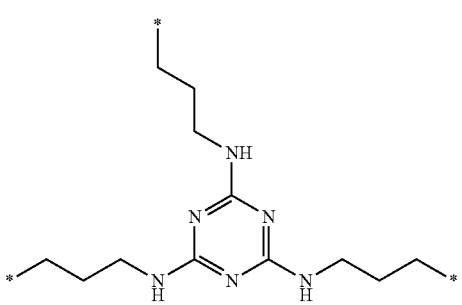

Linker2 independently represent
Linker2

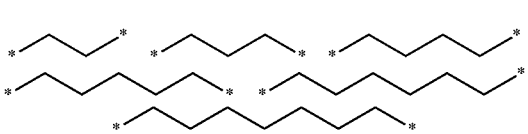

l, m, n, o represent integer varying from 1 to 100, preferably from 1 to 20.

The preferred branched units of the present invention are exampled in but not limited to the following examples;

Example 1

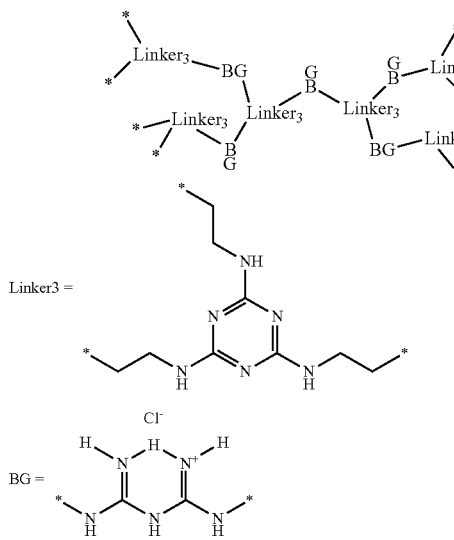

Example 2

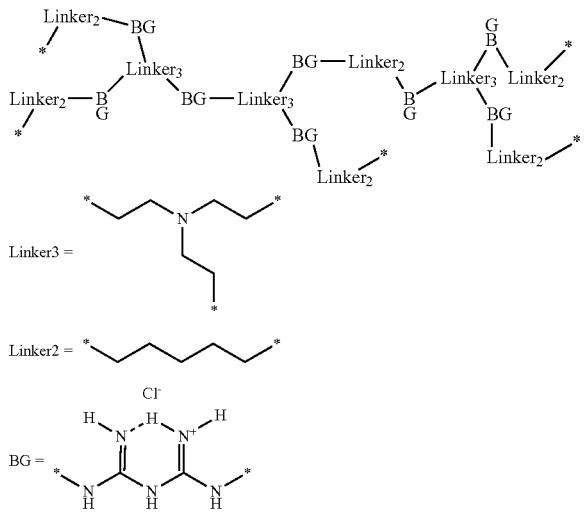

The biocides of the present invention have broad spectrum of antimicrobial activity and can be used in many applications including ophthalmic solutions. The ophthalmic solutions of the present invention can be formulated in various compositions, particularly as disinfectants in contact lens care products and as preservatives in cosmetic, ophthalmic, nasal or otic compositions, and are especially suitable for use in ophthalmic compositions such as artificial tears or topical ophthalmic pharmaceutical preparations. The types of compositions which may be preserved by the compounds of formula (I) include: ophthalmic pharmaceutical compositions, such as those described below; otic pharmaceutical compositions, such as topical compositions used in the treatment of bacterial infections or inflammation of the ear; dermatological compositions, such as anti-inflammatory compositions, as well as shampoos and other cosmetic compositions; and various other types of pharmaceutical compositions. In general, the polymers of the present invention will be present in the compositions at a concentration between about 0.00001 and 1.0 percent by weight/volume percent (w/v %). If used as a disinfectant, the polymers are preferably present at a concentration of between about 0.0005 and 0.5 w/v %; if used as a preservative; the polymers are present at a concentration between about 0.00005 and 0.05 w/v %. It is preferred that the polymers are present at a concentration of between 0.001 and 0.05 w/v % if used as a disinfectant and between 0.0001 and 0.01 w/v % if used as a preservative.

The compositions of the present invention may additionally contain other components, for example, buffers, tonicity adjusting agents, chelating agents, surfactants, solubilizers, active pharmaceutical agents, preservatives, pH adjusting agents and carriers.

In the case of contact lens and ophthalmic solutions, for example, various agents are added to enhance compatibility with the eye. To avoid stinging or irritation it is important that the solution possess a tonicity and pH within the physiological range, e.g., 200-350 mOsmole for tonicity and 6.5-8.5 for pH. To this end, various buffering and osmotic agents are often added. The simplest osmotic agent is sodium chloride since this is a major solute in human tears. In addition propylene glycol, lactulose, trehalose, sorbitol, mannitol or other osmotic agents may also be added to replace some or all of the sodium chloride. Also, various buffer systems such as citrate, phosphate (appropriate mixtures of $Na_2HPO_4$, $NaH_2PO_4$, and $KH_2PO_4$), borate (boric acid, sodium borate, potassium tetraborate, potassium metaborate and mixtures), bicarbonate, and tromethamine and other appropriate nitrogen-containing buffers (such as ACES, BES, BICINE, BIS-Tris, BIS-Tris Propane, HEPES, HEPPS, imidazole, MES, MOPS, PIPES, TAPS, TES, Tricine) can be used to ensure a physiologic pH between about pH 6.5 and 8.5. Borate and polyol systems may also be used to provide buffering, to enhance antimicrobial activity, or to provide both buffering and an enhancement of antimicrobial activity, or other useful properties to the compositions of the invention. The borate and polyol systems, which may be used, include those described in U.S. Pat. Nos. 6,849,253; 6,503,497; 6,365,636; 6,143,799; 5,811,466; 5,505,953; and 5,342,620; the entire contents of each are hereby incorporated into the present specification by reference.

The borates, which may be used in the compositions of the present invention, include boric acid and other pharmaceutically acceptable salts such as sodium borate (borax) and potassium borate. As used herein, the term "borate" refers to all pharmaceutically suitable forms of borates, as well as metaborates. Borates are common excipients in ophthalmic formulations due to good buffering capacity at physiological pH and well-known safety and compatibility with wide range of drugs and preservatives.

In addition to the compounds of formula (1, 2, 3, and 4) described above, the compositions of the present invention may contain one or more additional antimicrobial agent. The invention is not limited relative to the types of additional antimicrobial agent that may be utilized. The preferred biocides include: polyhexamethylene biguanide polymers ("PHMB"), polyquaternium-1, and the amino biguanides described in U.S. Pat. No. 6,664,294, the entire contents of which are hereby incorporated in the present specification by reference.

Amidoamines, amino alcohols, and borate/polyol complexes may also be utilized to enhance the antimicrobial activity of the compositions described herein. The preferred amidoamines are myristamidopropyl dimethylamine ("MAPDA") and related compounds described in U.S. Pat. No. 5,631,005 (Dassanayake, et al.). The preferred amino alcohols are 2-amino-2-methyl-1-propanol ("AMP") and other amino alcohols described in U.S. Pat. No. 6,319,464 (Asgharian). The entire contents of the '005 and '464 patents are hereby incorporated in the present specification by reference.

The following schemes further illustrate certain embodiments of the invention. These examples are provided to aid in the understanding of the invention and are not to be construed as limitations thereof.

Scheme 1

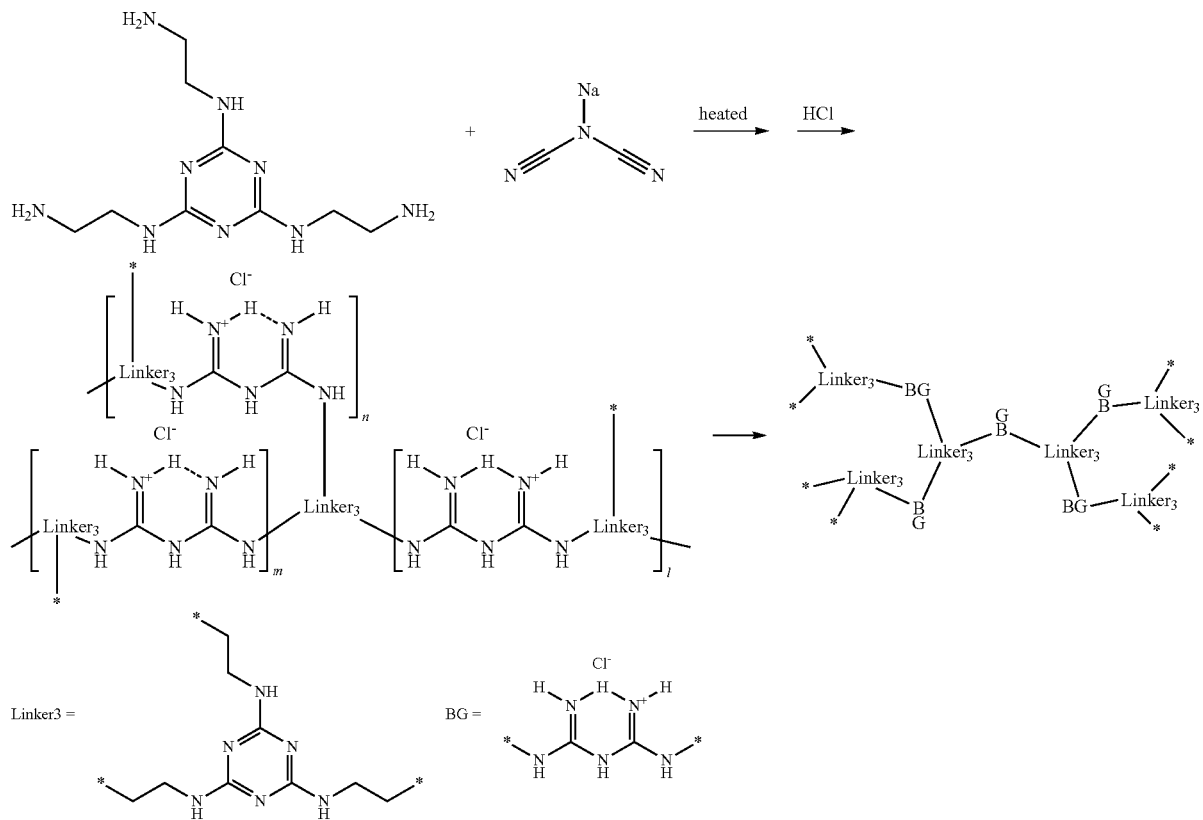

Scheme 2

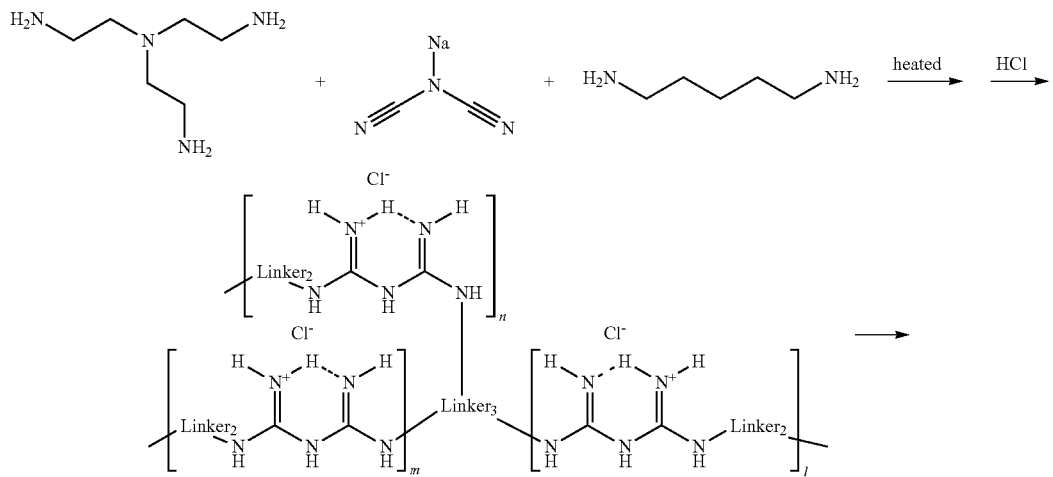

-continued

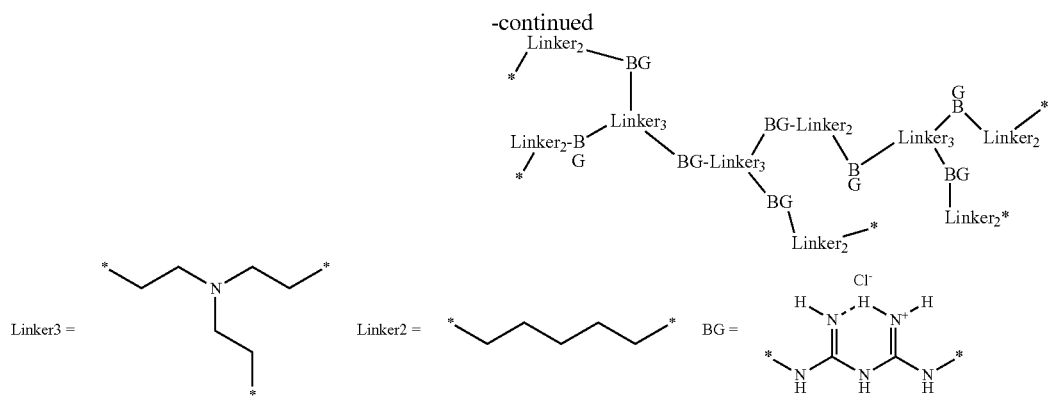

The polymer with the formula 2 was obtained by a synthetic method described below.

Compound 1. A mixture of tris(2-aminoethyl)amine-3 HCl (0.256 g, 1.0 mmol, 0.217 eq), 1,6-di($N^3$-cyano-$N^1$-guanidino)hexane (1.15 g, 4.60 mmol, 1.0 eq), hexane-1,6-diamine-2 HCl (0.567 g-0.1 g, 3.00 mmol, 0.65 eq) in 2-ethoxyethanol (3 mL) was heated at 165° C. for 10 min and 175° C. for 2 h. The milky suspension was added hexane-1,6-diamine-2 HCl (0.1 g) and heated at 155 C overnight. The mixture was cooled and turned into a two-layer liquid. The mixture was heated at 175° C. and monitored by NMR until the starting material disappeared. The solvent was distilled out and the residue was placed into vacuum to give a foamy-gummy solid. The solid was mixed with MeOH (4 mL) and precipitated with acetone to give a gum that was dried in vacuum to give the desired compound as foamy solid. NMR spectrum confirmed the structure of the product.

Compound 2. A mixture of tris(2-aminoethyl)amine-3 HCl (0.23 g, 0.90 mmol, 0.82 eq), 1,6-di($N^3$-cyano-$N^1$-guanidino)hexane (0.60 g, 2.4 mmol, 2.18 eq), polyhexanide (2.00 g, 1.10 mmol, 1.0 eq) was heated at 150 C for 3 h under nitrogen and tuned into a solid. The solid was crashed into powder, mixed with 2-methoxyethanol (3 mL) and was heated at 175° C. and monitored by NMR until the starting material disappeared. The solvent was evaporated by heating at 185° C. and the residue was dried in vacuum to give glassy solid. NMR spectrum confirmed the structure of the product.

Compound 3. A mixture of tris(2-aminoethyl)amine-3 HCl (0.35 g, 1.37 mmol, 1.25 eq), 1,6-di($N^3$-cyano-$N^1$-guanidino)hexane (0.60 g, 2.4 mmol, 2.18 eq), polyhexanide (2.00 g, 1.10 mmol, 1.0 eq) was heated at 150 C for 3 h under nitrogen and tuned into a solid. The solid was crashed into powder, mixed with 2-methoxyethanol (3 mL) and was heated at 175° C. and monitored by NMR until the starting material disappeared. The solvent was evaporated by heating at 185° C. and the residue was dried in vacuum to give glassy solid. NMR spectrum confirmed the structure of the product.

The antibacterial effectiveness testing of these samples and 2 standards was done against *C. alibicans* (ATCC 10231) as shown below.

| Sample ID | C. albicans ATCC 10231 Calculated Log | Log Recovery | Log Reduction |
| --- | --- | --- | --- |
| Polyhexanide A 1 ppm | 5.0 | <1.0 | >4.0 |
| Polyhexanide B 1 ppm | 5.0 | 1.5 | 3.5 |

| Sample ID | C. albicans ATCC 10231 Calculated Log | Log Recovery | Log Reduction |
| --- | --- | --- | --- |
| Compound 1 1 ppm | 5.0 | 2.0 | 3.0 |
| Compound 2 1 ppm | 5.0 | 2.5 | 2.5 |
| Polyhexanide A 5 ppm | 5.0 | 1.5 | 3.5 |
| Polyhexanide B 5 ppm | 5.0 | 1.0 | 4.0 |
| Compound 1 5 ppm | 5.0 | <1.0 | >4.0 |
| Compound 2 5 ppm | 5.0 | <1.0 | >4.0 |

What is claimed is:

1. A biocide solution comprise a polymer having at least one of branched biguanide units of the following formula:

Formular 1

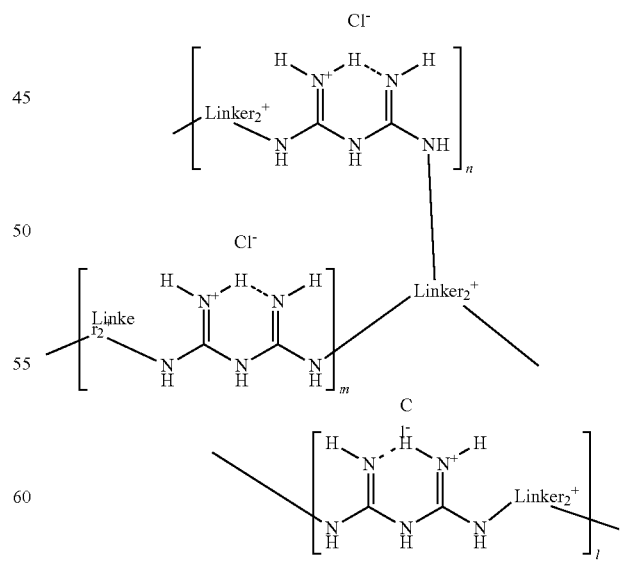

wherein Linker3+ represent linkage group with 3, or 4 points of connections for biguanide groups and at least 1% of Linkers has 3 or 4 connections;

Linker2+ represent independently the same or different linkage groups with 2, 3, or 4 points of connections for biguanide groups;

Linkers represent the sum of Linker3+ and Linker2+;

Linkers represent synthetic/non-natural linkage groups and has a molecular weight of less than 1000;

i, m, n represent integer varying from 1 to 100.

2. A biocide solution comprise a polymer according to claim 1 having at least one of branched biguanide units of the following units:

wherein Linker4 represent linkage group with 4 points of connections for biguanide groups and at least 1% of Linkers has 4 points of connections in Formular 2;

Linker3 represent linkage group with 3 points of connections for biguanide groups and at least 1% of the Linkers has 3 or more connections in Formular 3;

PS Linker2 represent independently the same or different linkage groups with 2 points of connections for biguanide groups;

Formular 2

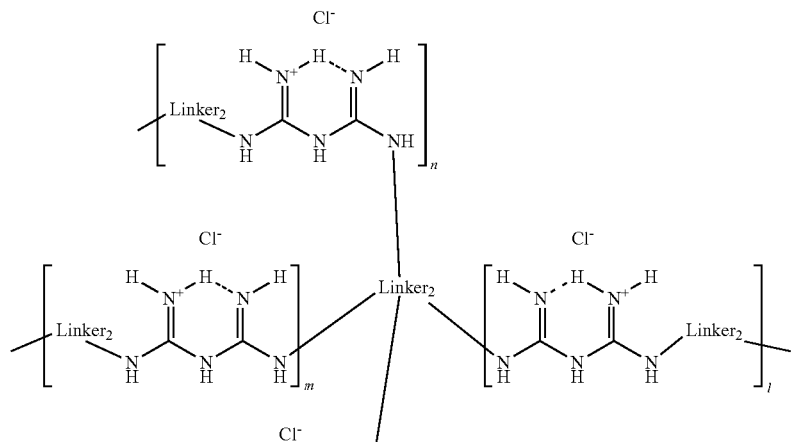

Formular 3

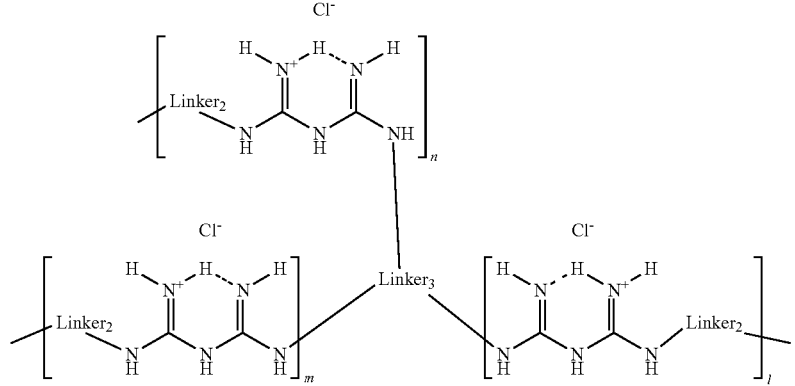

Formular 4

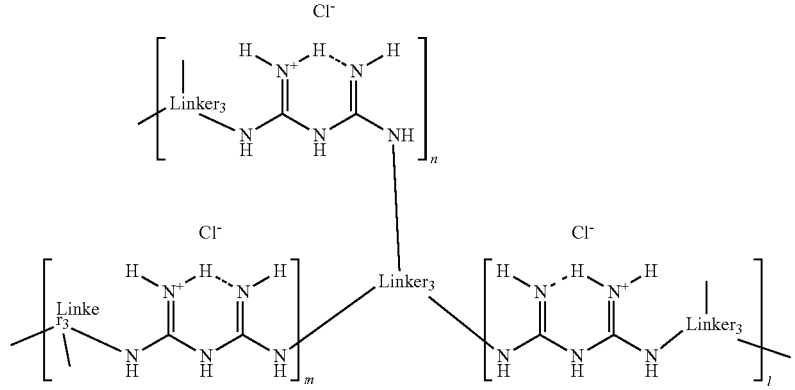

Linkers represent the sum of Linker4, Linker3, and Linker2;

Linker4 independently represent

Linker4

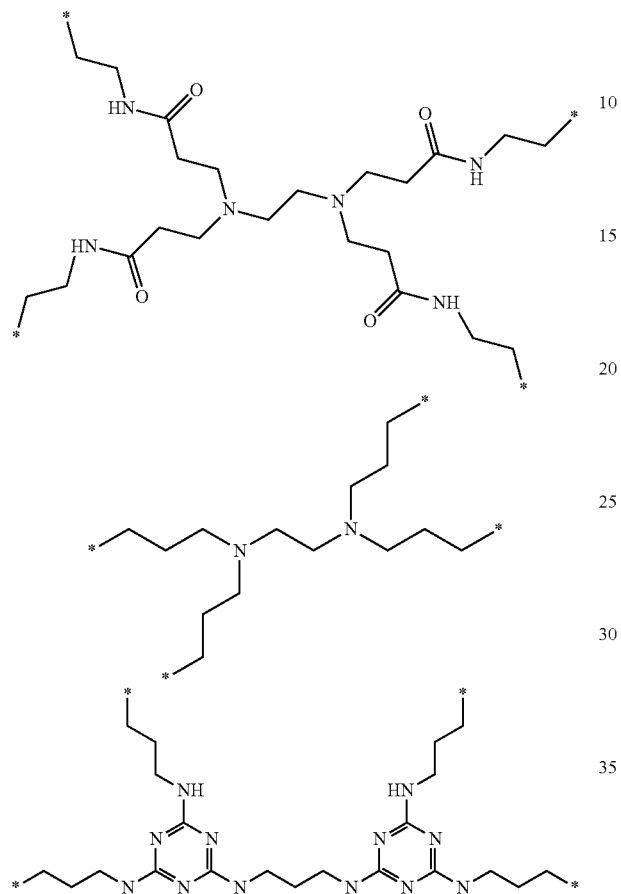

Linker3 independently represent

Linker3

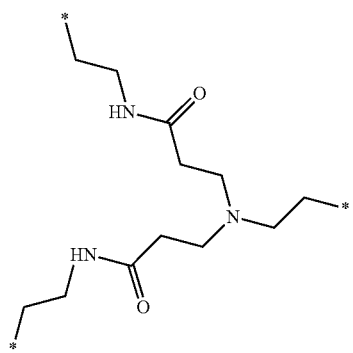

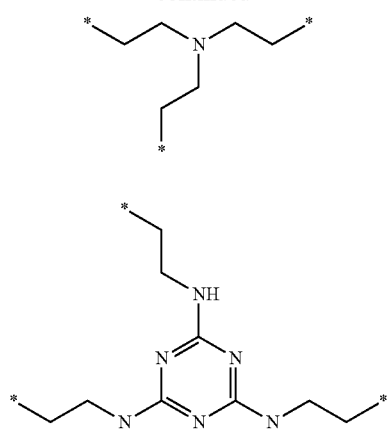

Linker2 independently represent

Linker2

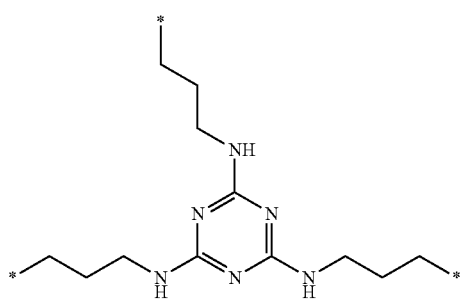

i, m, n, o represent integer varying from 1 to 100.

3. A pharmaceutical composition comprising a preservation-effective amount of a polymer according to claim 2.

4. A biocide solution of claim 2, wherein the composition may contain one or more additional antimicrobial agent, for example but not limited to, polyhexamethylene biguanide polymers ("PHMB"), polyquaternium-1, myristamidopropyl dimethylamine (Aldox), and amino biguanides.

5. A biocide solution of claim 2, wherein the concentration of the polymer in the ophthalmic solution ranges from 0.0001 to 3.0 w/v %.

6. A pharmaceutical composition comprising a preservation-effective amount of a polymer according to claim 1.

* * * * *